(12) United States Patent  (10) Patent No.: US 8,808,340 B1
Jurbala  (45) Date of Patent: Aug. 19, 2014

(54) DEVICE FOR REPAIRING A BONE FRACTURE

(75) Inventor: Brian M. Jurbala, Lakeland, FL (US)

(73) Assignee: SonicSurg Innovations, LLC, Lakeland, FL (US)

( * ) Notice: Subject to any disclaimer, the term of this patent is extended or adjusted under 35 U.S.C. 154(b) by 554 days.

(21) Appl. No.: 13/098,978

(22) Filed: May 2, 2011

Related U.S. Application Data

(60) Provisional application No. 61/329,636, filed on Apr. 30, 2010.

(51) Int. Cl.
*A61B 17/84* (2006.01)

(52) U.S. Cl.
USPC ............................ 606/326; 606/90; 606/99

(58) Field of Classification Search
USPC ............................................. 606/90, 99, 326
See application file for complete search history.

(56) References Cited

U.S. PATENT DOCUMENTS

| | | | |
|---|---|---|---|
| 6,039,761 A * | 3/2000 | Li et al. ..................... | 623/17.16 |
| 6,190,414 B1 * | 2/2001 | Young et al. ............... | 623/17.15 |
| 6,193,757 B1 * | 2/2001 | Foley et al. ................ | 623/17.16 |
| 6,379,359 B1 | 4/2002 | Dahners | |
| 6,428,540 B1 | 8/2002 | Claes et al. | |
| 6,669,699 B2 * | 12/2003 | Ralph et al. ................ | 606/90 |
| 6,743,255 B2 * | 6/2004 | Ferree ........................ | 623/17.11 |
| 7,044,971 B2 * | 5/2006 | Suddaby ..................... | 623/17.15 |
| 7,625,377 B2 * | 12/2009 | Veldhuizen et al. ........ | 606/90 |
| 7,901,409 B2 * | 3/2011 | Canaveral et al. .......... | 606/86 R |
| 2004/0111090 A1 | 6/2004 | Dahners | |
| 2005/0165395 A1 | 7/2005 | Orbay et al. | |
| 2006/0149257 A1 | 7/2006 | Orbay et al. | |
| 2006/0200157 A1 | 9/2006 | Orbay et al. | |
| 2007/0191855 A1 | 8/2007 | Orbay et al. | |
| 2008/0161805 A1 | 7/2008 | Saravia et al. | |
| 2009/0054900 A1 | 2/2009 | Rabiner et al. | |
| 2009/0182336 A1 | 7/2009 | Brenzel et al. | |
| 2009/0216230 A1 | 8/2009 | Pizarro | |

FOREIGN PATENT DOCUMENTS

| | | |
|---|---|---|
| IE | 20050638 A1 | 4/2007 |
| WO | 2008109566 A1 | 9/2008 |

* cited by examiner

*Primary Examiner* — Nicholas Woodall
(74) *Attorney, Agent, or Firm* — Michele L. Lawson; Smith & Hopen, P.A.

(57) ABSTRACT

A device for repairing a bone fracture that is inserted intrafocally and deployed to properly position the facture. The device includes an implant inserted intrafocally as a low profile fold and is then deployed to positione the fracture.

2 Claims, 5 Drawing Sheets

DEVICE FOR REPAIRING A BONE FRACTURE

CROSS REFERENCE TO RELATED APPLICATION

This application claims priority to currently pending U.S. Prov. Pat. Appl. No. 61/329,636, entitled "DEVICE AND METHOD FOR REPAIRING A BONE FRACTURE," filed on Apr. 30, 2010, the contents of which are hereby incorporated by reference.

BACKGROUND OF THE INVENTION

1. Field of the Invention

This invention relates to a device for repairing a bone fracture. More specifically, it relates to a device that is inserted intrafocally into a fracture and deployed to properly position the fracture.

2. Description of the Related Art

Reduction is a medical procedure to restore a fracture to the correct alignment. When a bone fractures, the fragments lose their alignment in the form of displacement or angulation. For the fractured bone to heal without any deformity, the bony fragments must be re-aligned to their normal anatomical position. Orthopedic surgeons attempt to recreate the normal anatomy of the fractured bone by reduction.

Bone fracture repair is surgery to fix a broken bone using plates, nails, screws, or pins. Putting a fracture back in place normally requires a large open incision and a large plate or intramedullary device to hold the reduction. For some fractures (i.e., distal radius fractures) percutaneous pins are used to reduce and secure the fracture. Percutaneous pins can be used as levers to position a fracture and fixate it with minimal or no incisions; however, this method only offers tentative fixation at best and many times the pins have to be left out of the skin, exposing the patient to the risk of infection. In addition, using the pin as both a lever and as a fixation device is imprecise and often leads to inadequate reduction and fixation of the fracture.

Many surgeons rely on external fixation devices to distract the fracture from the outside through traction and then hold the reduction until healing takes place over 6 to 8 weeks. These devices are imprecise and contain pins that protrude through the skin and can potentially damage nerves and vessels and lead to joint stiffness. In addition, as mentioned above, these pins protrude out of the skin for weeks exposing the patient to the risk of infection. External fixation devices are an indirect method of reduction and often lead to loss of reduction and inferior results.

Open plating relies on the surgeon getting a reduction by external fixation and/or external distraction (with the disadvantages noted above) or by sticking a pin or lever in the fracture to push it back in place and disimpact it. The fracture is then pinned to temporarily hold the fracture in place. The surgeon puts a locking plate on the bone with screws to hold the fracture until it heals. This method creates a large incision, causing the patient more pain and relies on the above mentioned methods to reduce the fracture prior to plating.

Intrameduallry devices currently available, like the plates, only allow the fracture to be held in place once reduced by the indirect methods noted above. Current intrameduallry devices have not been shown to be an effective means of both reducing and securing the fracture.

What is needed is a single device for both reducing and securing the fracture.

What is also needed is a small narrow device that can be inserted intrafocally into a fracture and then deployed to reduce (put back in place) an impacted fracture in a controlled fashion.

However, in view of the prior art considered as a whole at the time the present invention was made, it was not obvious to those of ordinary skill in the art how the limitations of the art could be overcome.

SUMMARY OF THE INVENTION

Generally speaking, the claimed invention is a device that is inserted intrafocally into a fracture as a low profile fold and then deployed to create a rigid construct to reduce (put back in place) an impacted fracture in a controlled fashion.

In a first embodiment, the device includes at least two support bars and a lever forming an implantable rigid construct. The support bars are hingedly connected together and the lever is hingedly connected to one of the support bars. The lever acts as a pawl in communication with a plurality of ratchet like teeth disposed along the support bar opposite the lever thereby forming a pawl and ratchet type mechanism for ratcheting open the support bars.

To insert the support bars and lever into a fracture, a detachable handheld assembly is used. The detachable assembly includes an elongate base, an elongate support rod, an elongate control rod, a control knob, and an elongate control slot. The elongate base is adapted to be held in a human hand and includes a hollow interior. The elongate support rod includes a proximal end attached to the elongate base and a distal end that extends distally of the elongate base and is detachably connected to the support bars. The elongate control rod includes a proximal end slideably disposed in the hollow interior of the elongate base and a distal end that extends distally of the elongate base and is detachably connected to the lever. The control knob is connected to the elongate control rod and is slideably mounted on the elongate base for controlling the instantaneous position of the elongate control rod. The elongate control slot is formed in the elongate base, with the elongate control rod being connected to the control knob through the elongate control slot.

The control knob and the elongate control rod include a first position where the support bars and the lever are in a collapsed folded repose position. Conversely, the control knob and the elongate control rod include a second position where the support bars and the lever form a triangular support structure as the lever is ratcheted upward. In both positioned, the elongate support rod includes a respective fixed position unaffected by retraction and extension of the control knob and the elongate control rod.

In practice, the elongate base is held in the hand of a user. The user manipulates the control knob to retract the control rod. As the control rod is contracted, it pulls on the lever and extends it upward from its first folded position. As the lever extends upward, it is incrementally secured in place via the ratchet type mechanism the lever forms with the plurality of ratchet like teeth disposed along the support bar opposite the lever. As the lever is ratcheted up, it forms a rigid construct with the support bars to reduce an impacted fracture in a controlled fashion. The control rod and support rod are then detached from the lever and support bars, respectively, leaving the construct within the fracture site.

In a second embodiment, the device includes a toggle screw type support forming an implantable rigid construct. This embodiment further includes an elongate base and an elongate support rod for inserting the toggle screw type support into a fracture site. Specifically, the elongate base is adapted to be held in a human hand, with the elongate support rod having a proximal end detachably connected to the elongate base and a distal end that extends distally of the elongate base. The support rod includes external threads that engage the toggle screw type support.

The toggle screw type support includes two support bars hingedly connected and a toggle lever disposed between the support bars. The toggle lever includes a hole with internal threads that correspond to the external threads of said support rod. The toggle screw type support includes a first position where the toggle screw type support is folded for insertion into the fracture site. The toggle screw type support also includes a second position where the toggle screw type support is open position forming a support structure when the elongate support rod is threaded through the corresponding internal threads of the toggle screw type support.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
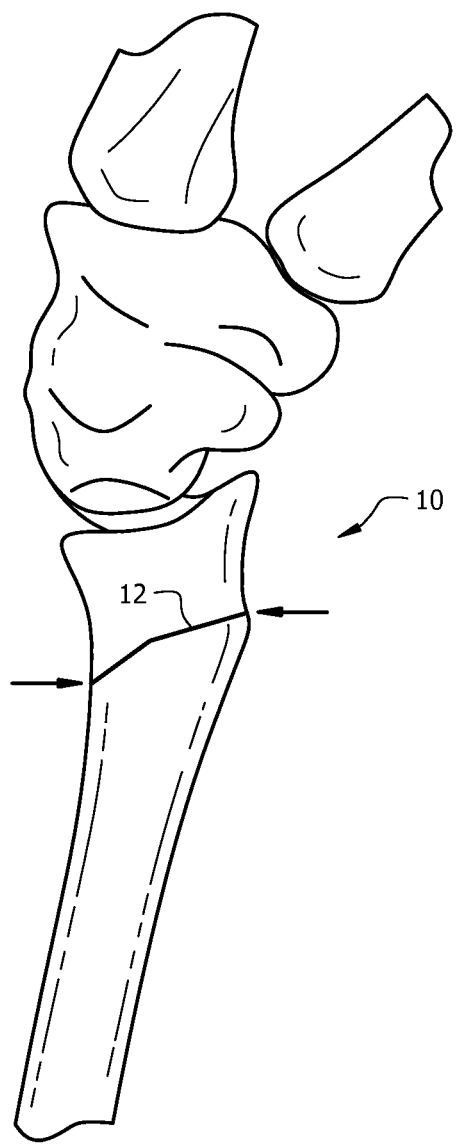
FIG. 1 is a bone with a fracture having displacement or angulation.

As depicted in FIG. 1, a bone 10 includes a fracture 12. When a bone fractures, the fragments lose their alignment in the form of displacement or angulation. For the fractured bone to heal without any deformity, the bony fragments must be re-aligned to their normal anatomical position. The claimed invention is bone fracture repair device that is inserted intrafocally into a fracture as a low profile fold and then deployed to create a rigid construct support to reduce an impacted fracture in a controlled fashion.

Figure 2:
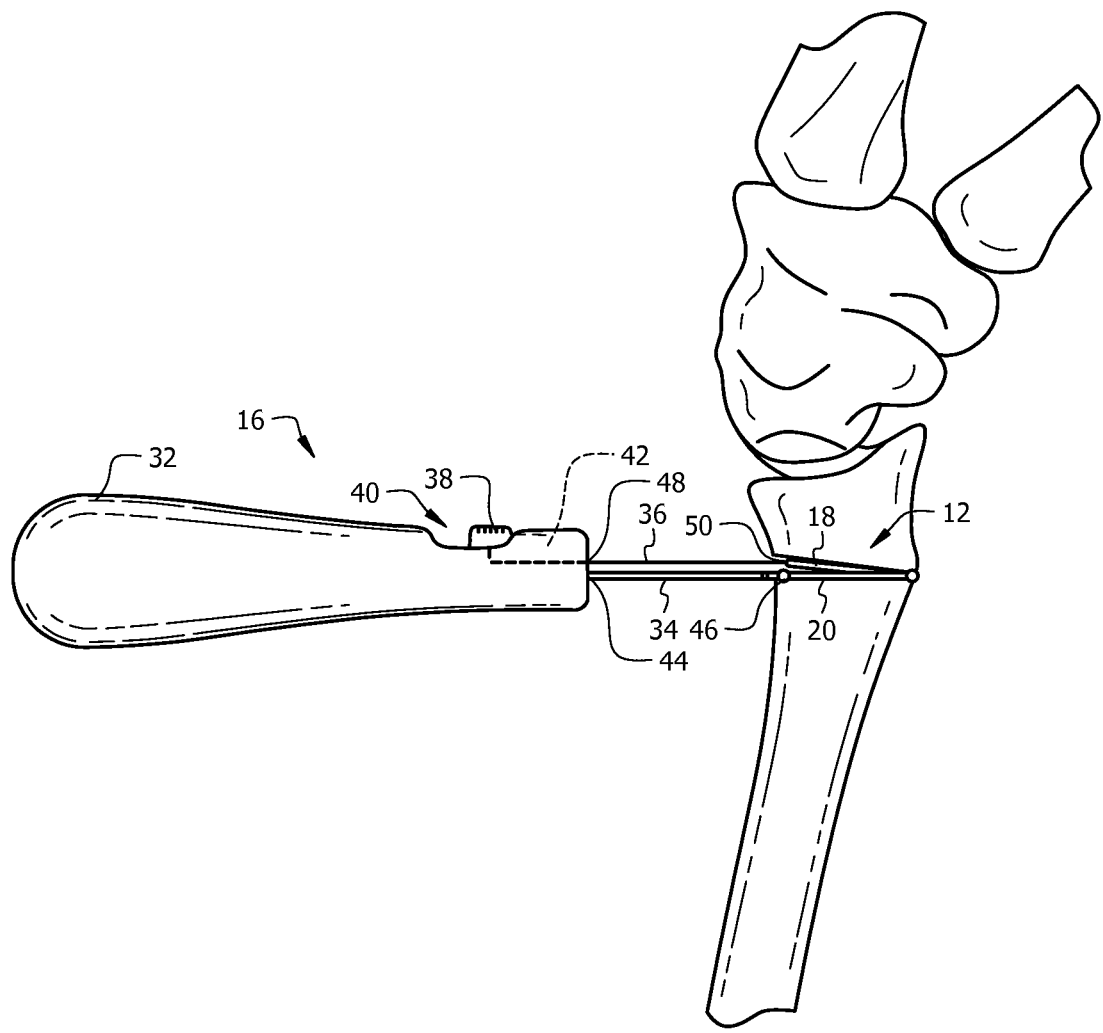
FIG. 2 is a bone fracture repair device in a first folded position.
Figure 3:
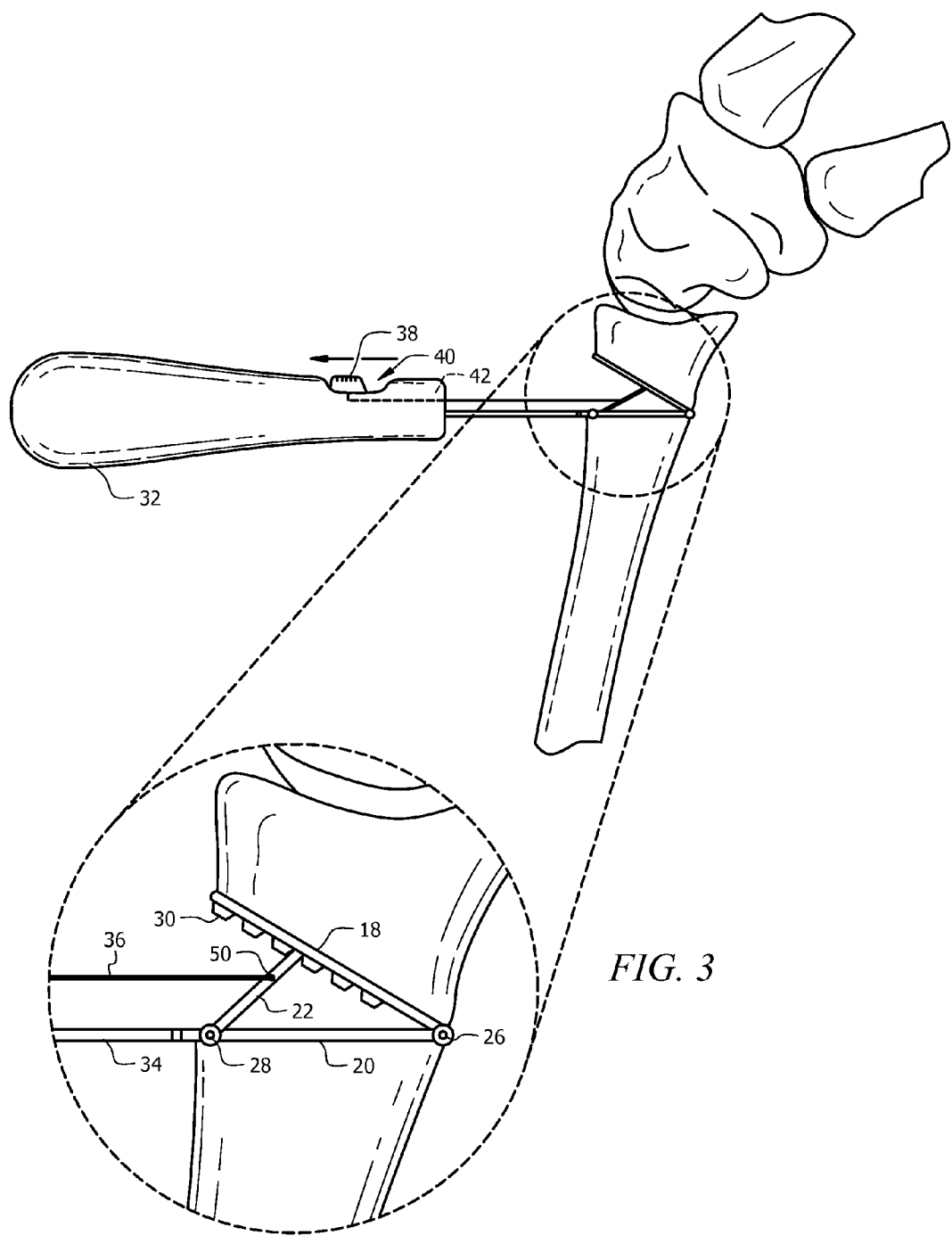
FIG. 3 is the bone fracture repair device in a second open position.
Figure 4:
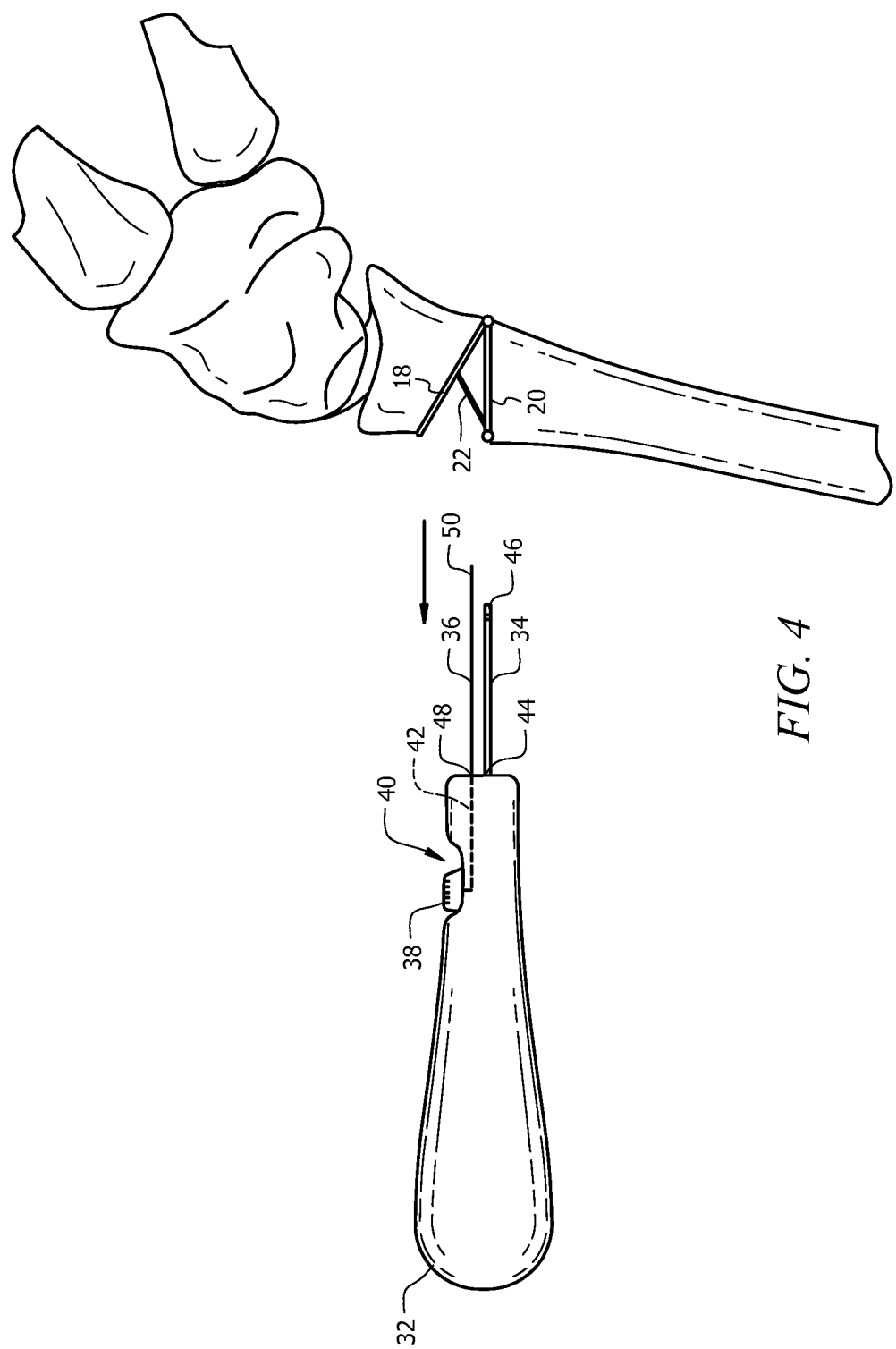
FIG. 4 depicts a control rod and a support rod detached from a construct within the fracture.

In a first embodiment, as depicted in FIGS. 2-4, the device includes a first low profile folded position (FIG. 2) that is inserted into the fracture 12 using a detachable assembly 16. The implantable portion of the device includes two support bars 18 and 20 and a lever 22 forming an implantable rigid construct. The support bars 18 and 20 are hingedly connected 26 together and the lever 22 is hingedly connected 28 to one of the support bars 20.

As depicted in FIG. 3, the lever 22 acts as a pawl in communication with a plurality of ratchet like teeth 30 disposed along the support bar 18 opposite the lever 22 thereby forming a pawl and ratchet type mechanism for ratcheting open the support bars 18 and 20. As the support bars 18 and 20 are ratcheted open, they reduce the fracture to its original angulation. Although depicted as a ratchet type mechanism, any mechanism that creates the triangle and locks it from sliding from closed is envisioned.

Referring again to FIGS. 2-4, the detachable assembly includes an elongate base 32, an elongate support rod 34, an elongate control rod 36, a control knob 38, and an elongate control slot 40. The elongate base 32 is adapted to be held in a human hand and includes a hollow interior 42. The elongate support rod 34 includes a proximal end 44 attached to the elongate base 32 and a distal end 46 that extends distally of the elongate base 32 and is detachably connected to the support bar 20. The elongate control rod 36 includes a proximal end 48 slideably disposed in the hollow interior 42 of the elongate base 32 and a distal end 50 that extends distally of the elongate base 32 and is detachably connected to the lever 22. The control knob 38 is connected to the elongate control rod 36 and is slideably mounted on the elongate base 32 for controlling the instantaneous position of the elongate control rod 36. The elongate control slot 40 is formed in the elongate base 32, with the elongate control rod 36 being connected to the control knob 38 through the elongate control slot 40.

As depicted in FIGS. 2 and 3, the control knob 38 and the elongate control rod 36 include a first position (FIG. 2) where the support bars 18 and 20 and the lever 22 are in a collapsed folded repose position. Conversely, as depicted in FIG. 3, the control knob 38 and the elongate control rod 36 include a second position where the support bars 18 and 20 and the lever 22 form a triangular support structure as the lever 22 is ratcheted upward. In both positioned, the elongate support rod 34 includes a respective fixed position unaffected by retraction and extension of the control knob 38 and the elongate control rod 36.

As depicted in FIG. 4, once the implantable portion of the device is positioned within the fracture, the control rod 36 and support rod 34 are detached from the lever 22 and support bars 20, respectively, leaving the construct within the fracture site.

The elongate base and support rod give control and leverage to a surgeon as they insert the implant intrafocally. Once within the fracture, the control rod attached to the folded down lever bar is pulled and through a series ratchet teeth (or any catching or locking type mechanism) on the support structure is deployed to create a rigid construct support to reduce an impacted fracture in a controlled fashion.

The claimed invention allows for both the reduction and secure fixation of the fracture with one device. It is as minimally invasive as the percuateous intrafocal pinning method but has the advantage of being more controlled and precise and allows the surgeon to achieve a reduction and hold it securely with one implant. The implant is contained completely or nearly completely within the fracture site and under the skin reducing the infection risks associated with external fixation and percutaneous intrafocal pinning.

Unlike plating, there is no large incision required. Similarly, unlike both plating and intrameduallry, fixation of the device allows a surgeon to fixate the fracture in one position reduce the fracture back into place and securely holding it.

The claimed invention can be attached to a plate to provide a more secure fracture fixation. Moreover, a plurality of the implants may be stacked to distract a fracture even further.

The implant is not limited to three bars linked by hinges; instead, the implant may include a plurality of bars hingedly connected.

Ridges or short spike like protrusions may be placed on the bars for additional traction and friction. The device may also be cannulated to aid in more accurate placement over a k-wire. Furthermore, the distal end of the implant may have a protruding screw or spike to fix it to the far side of the bone for added stability.

The device can be used alone or in combinations with plates, screws, or pins. It can attach to a plate making a construct that can both reduce and fixate a fracture. In addition, the device can be used in combination with biologic bone cement materials to provide a better reduction and reinforced construct to fix a fracture.

Figure 5:
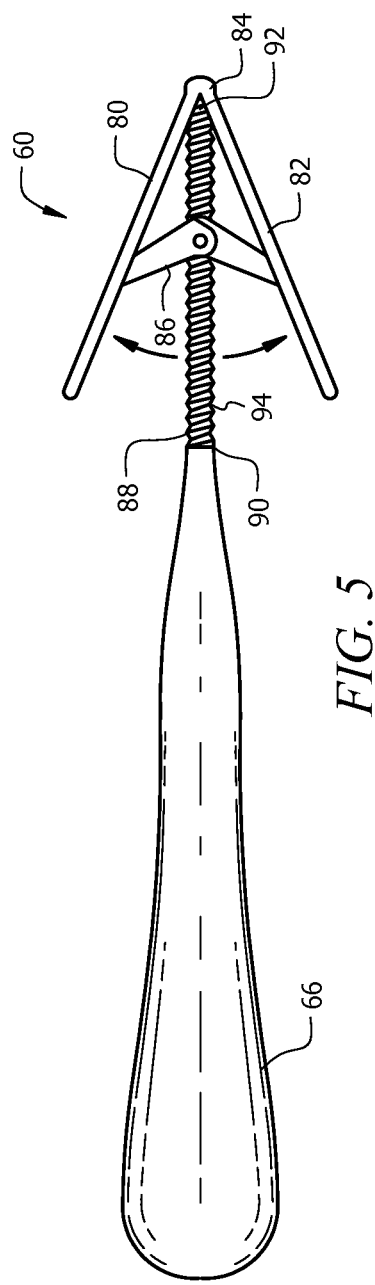
FIG. 5 is a toggle screw type support.

In a second embodiment, as depicted in FIG. 5, the implantable portion of the device may include a toggle screw type support 60. The toggle screw type support 60 includes two support bars 80 and 82 hingedly connected 84 and a toggle lever 86 disposed between the support bars 80 and 82. The toggle lever 86 includes a hole with internal threads that correspond to the external threads 94 a support rod 88. The toggle screw type support 60 includes a first position where it is folded for insertion into the fracture site and a second position where it is open forming a support structure when the elongate support rod 88 is threaded through the corresponding internal threads of the toggle lever 86. An elongate base 66 is adapted to be held in a human hand, with the elongate support rod 88 having a proximal end 90 detachably connected to the elongate base and a distal end 92 that extends distally of the elongate base.

Both implantable constructs may include support bars that are shaped in an arching fashion to provide additional stability and support. The support bars, however, can be flat, round, or of any desired shape.

The device can be used safely through a small incision for a slow controlled and stable fracture reduction, allowing a surgeon to fix fractures safely, effectively, and with less pain in the emergency room or office environment under a local or block anesthetic.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A device for repairing a bone fracture, comprising:
   at least two support bars hingedly connected;
   a lever bar hingedly connected to one of said at least two support bars, said lever bar being a pawl in communication with a plurality of ratchet like teeth disposed along one of said at least two support bars opposite said lever bar thereby forming a pawl and ratchet type mechanism for ratcheting open said at least two support bars;
   an elongate base adapted to be held in a human hand, said elongate base having a hollow interior;
   an elongate support rod having a proximal end attached to said elongate base and having a distal end that extends distally of said elongate base and is detachably connected to said at least two support bars;
   an elongate control rod having a proximal end slideably disposed in said hollow interior of said elongate base and having a distal end that extends distally of said elongate base and is detachably connected to said lever bar;
   a control knob connected to said elongate control rod, said control knob being slideably mounted on said elongate base for controlling the instantaneous position of said elongate control rod;
   an elongate control slot formed in said elongate base, said elongate control rod being connected to said control knob through said elongate control slot;
   said control knob and said elongate control rod having a first position where said at least two support bars and said lever are in a collapsed repose position;
   said control knob and said elongate control rod having a second position where said at least two support bars and said lever form a triangular support structure; and
   said elongate support rod having a respective fixed position unaffected by retraction and extension of said control knob and said elongate control rod.

2. A device for repairing a bone fracture as in claim 1, further comprising:
   said control rod being a string, wire, suture, or additional bar.

* * * * *